US008110074B1

(12) United States Patent
Neckers

(10) Patent No.: US 8,110,074 B1
(45) Date of Patent: Feb. 7, 2012

(54) PHOTOCHEMICAL METHOD FOR PRODUCING HYDROCARBONS

(76) Inventor: Douglas C. Neckers, Perrysburg, OH (US)

(*) Notice: Subject to any disclaimer, the term of this patent is extended or adjusted under 35 U.S.C. 154(b) by 1527 days.

(21) Appl. No.: 11/540,906

(22) Filed: Sep. 29, 2006

Related U.S. Application Data

(60) Provisional application No. 60/723,286, filed on Oct. 3, 2005.

(51) Int. Cl.
*C07C 1/00* (2006.01)
(52) U.S. Cl. ................................. 204/157.15
(58) Field of Classification Search ............. 204/157.15, 204/157.6, 157.68, 157.87
See application file for complete search history.

(56) References Cited

U.S. PATENT DOCUMENTS

| | | | |
|---|---|---|---|
| 2,197,709 A | 4/1940 | Ralston et al. ............... | 260/592 |
| 2,369,919 A | 2/1945 | Sauer .......................... | 260/550 |
| 2,773,904 A * | 12/1956 | Silverstein .................. | 568/319 |
| 3,865,855 A * | 2/1975 | Linn et al. .................... | 554/159 |
| 4,094,756 A * | 6/1978 | Taylor .......................... | 522/33 |
| 4,849,076 A | 7/1989 | Neckers ................... | 204/157.15 |
| 6,004,914 A | 12/1999 | Percella et al. .............. | 510/126 |
| 6,200,938 B1 | 3/2001 | Percella et al. .............. | 510/126 |
| 6,310,002 B1 | 10/2001 | Krzoska et al. .............. | 503/213 |
| 6,369,007 B1 | 4/2002 | Percella et al. .............. | 510/130 |
| 2004/0235691 A1 | 11/2004 | Pham et al. ................... | 510/130 |
| 2005/0037045 A1 | 2/2005 | Henderson et al. ........... | 424/210 |
| 2005/0108924 A1 | 5/2005 | Krull ............................. | 44/393 |
| 2005/0126070 A1 | 6/2005 | Krull ............................. | 44/393 |

FOREIGN PATENT DOCUMENTS

GB 264862 1/1927

OTHER PUBLICATIONS

Neckers, "Developmental Photochemistry. The Norrish Type II Reaction", J. Org. Chem. (no month, 1971), vol. 36, No. 13, pp. 1838-1840.*
Kell et al., "Norrish Type II Photochemical Reaction of an Aryl Ketone on a Monolayer-Protected Gold Nanocluster. Development of a Probe of Conformational Mobility", Org. Lett. (no month, 2000), vol. 2, No. 21, pp. 3381-3384.*
Erdemoglu et al., "Effect of Irrigation on the Oil Content and Fatty Acid Composition of Some Sunflower Seeds", Chem. of Natural Compds. (no month, 2003), vol. 39, No. 1, pp. 1-4.*
Kropf, H. et al., "Organische Peroxide—X'," Tetrahedron, vol. 30, pp. 2943-2948 (1974).
Lee, S.H. et al., "Dioxododecenoic Acid: A Lipid Hydroperoxide-Derived Bifunctional Electrophile Responsible for Etheno DNA Adduct Formation," Chem. Res. Toxicol., 18, pp. 566-578 (2005).
Haslbeck, F. et al, "Formation of Hydroperoxides with Unconjugated Diene Systems During Autoxidation and Enzymic Oxygenation of Linoleic Acid," Biochimica et Biophysica Acta, 750, pp. 185-193 (1983).
Akiyama, S. et al., "Reversal of Stereospecificity during Allylic Hydroperoxidation of 3-Norcarene and Bicyclo[oct-3-ene Derivatives Arising from Structurally Enforced Quenching of Singlet Oxygen by the Hydrazide Functionality," Journal of the American Chemical Socity, 98:20, pp. 6412-6413 (Sep. 1976).
Lederer, M., "Addition von Hydroperoxiden an N-Vinylverbindungen," Chem. Ber., 105, p. 2169-2174 (1972).
Norton, Charles J., "In Situ Olefin-Derived Peroxides—Effectiveness for Initiating Radical Addition and Polymerization Reactions," Ind. Eng. Chem. Prod. Res. Develop., vol. 11, No. 1, pp. 27-35 (1972).
Haubenstock, H. et al, "Stereochemistry of the Addition of t-Butyl Hydroperoxide to Cyclopentadiene," J. Org. Chem., vol. 35, No. 10, pp. 3208-3210 (1970).
Neckers, D.C. et al., "Developmental Photochemistry. The Norrish Type II Reaction," J. Org. Chem., vol. 36, No. 13, pp. 1838-1840 (1971).
Lewis, N. S., "Chemical Challenges in Renewable Energy," Division of Chemistry and Chemical Engineering, California Institute of Technology (date unknown).
Gilbert, A. et al., *Essentials of Molecular Photochemistry*, CRC Press, pp. 310-330 (date of first publication unknown).
Yu, J-Q et al., "Diverse Pathways for the Palladium(II)-Mediated Oxidation of Olefins by tert-Butylhydroperoxide," Organic Letters, vol. 4, No. 16, pp. 2727-2730 (2002).
Crich, D. et al., "Catalytic Allylic Oxidation with a Recyclable, Fluorous Selenic Acid," Organic Letters, No. 6, No. 5, pp. 775-777 (2004).
Catino, A.J., "Dirhodium(II) Caprolactamate: An Exceptional Catalyst for Allylic Oxidation," J. Am. Chem. Soc., 126, pp. 13622-13623 (2004).
*Organic Reactions*, vol. III, John Wiley & Sons, Inc., pp. 1-16 and 316-317 (date of first publication unknown).
*Organic Reactions*, vol. V, John Wiley & Sons, Inc., pp. 229-242 (date of first publication unknown).
*Friedel-Crafts and Related Reactions*, I—General Aspects, Interscience Publishers, a division of John Wiley & Sons, pp. xv and xvii (1963).
*Friedel-Crafts and Related Reactions*, III—Acrylation and Related Reactions, Interscience Publishers, a division of John Wiley & Sons, pp. xiii-xiv (1964).
*Synthetic Organic Chemistry*, John Wiley & Sons, Inc., pp. 479-480 (date of first publication unknown).
Ralston, A.W. et al., "Fatty-Acyl-Modified Resins—Dicyclopentadiene, Coumarone, and Indene Types," Industrial and Engineering Chemistry, vol. 32, No. 1, pp. 99-101 (Jan. 1940).
Justik, M.W. et al., "Oxidative rearrangements of arylalkenes with [hydroxy(tosyloxy)iodo]benzene in 95% methanol: a general, regiospecific synthesis of α-aryl ketones," Tetrahedron Letters, 45, pp. 6159-6163 (2004).
Miyano, M. et al., "(Acyloxy)benzophenones and (Acyloxy)-4-pyrones. A New Class of Inhibitors Human Neutrophil Elastrase," J. Med. Chem., 31, pp. 1052-1061 (1988).
Swann, Jr., S et al., "Thoria Aërogel Catalyst: Aliphatic Esters to Ketones," Ind. Eng. Chem., 26, No. 9, pp. 1014 (1934).
*Mechanistic Organic Photochemistry*, Reinhold Publishing Corporation, pp. 182-184 (date of first publication unknown).

(Continued)

*Primary Examiner* — Edna Wong
(74) *Attorney, Agent, or Firm* — Thompson Hine LLP

(57) ABSTRACT

The present invention relates to a method of using radiation and (in one embodiment) solar energy and UV radiation to convert natural products, for example derivatives of vegetable oils, to lower molecular weight hydrocarbons. The invention further relates to a process whereby these hydrocarbons can be converted to vinyl monomers and used in the formation of plastics, solvents, fuels and the like.

33 Claims, No Drawings

OTHER PUBLICATIONS

Day, M. et al, "The Norrish Type II Photodecomposition of Di-n-Butyl Terephthalate," Canadian Journal of Chemistry, vol. 49, pp. 2916-2917 (1971).

Mellier, D. et al., "Etude Du Mecanisme De La Photolyse D'Esters Et D'Amides: Influence De La Nature Du Groupe Acide Sur Le Cours De La Reaction," Tetrahedron Letters, No. 47, pp. 4559-4562 (1971).

Coyle, J.D. et al, "Photoelimination in N-Substituted Benzamides," Tetrahedron Letters, No. 49, pp. 4525-4528 (1976).

Aoyama, H. et al., "Photochemical Reactions of α-Oxo Amides. Norrish Type II Reactions via Zwitterionic Intermediates," J. Am. Chem. Soc, 105, pp. 1958-1964 (1983).

Do, C.H. et al., "FT-IR Spectroscopic Study on the Photo- and Photooxidative Degradation of Nylons," Journal of Polymer Science: Part A: Polymer Chemistry, vol. 25, pp. 2301-2321 (1987).

Scaiano, J.C., "Laser Flash Photolysis Studies of the Reactions of Some 1,4-Biradicals," Acc. Chem. Res., 15, pp. 252-258 (1982).

Coyle, J.D., "Photochemistry of Carboxylic Acid Derivatives," Chemical Reviews, vol. 78, No. 2, pp. 97-123 (1978).

Butkus, E. et al., "Synthesis and Redox Properties of Ferrocene Derivatives containing an Oleyl Group," J. Chem. Research, (S), pp. 722-723 (1998).

Conrad II, P.G. et al., "New Phototriggers: Extending the p-Hydroxyphenacyl π-π* Absorption Range," Organic Letters, vol. 2, No. 11, pp. 1545-1547 (2000).

Wood, T.F. et al., "The Cyclo-Addition of 1,3-Butadienes to Aromatic Hydrocarbons to Form Indans," Tetrahendron Letters, No. 1, pp. 1-8 (1963).

* cited by examiner

PHOTOCHEMICAL METHOD FOR PRODUCING HYDROCARBONS

CROSS REFERENCE TO RELATED APPLICATIONS

The present application claims priority of U.S. Provisional Application No. 60/723,286 filed Oct. 3, 2005.

DEFINITIONS

Fatty acid—any of the several long alkyl chain acids found in essential oils. A table of those identified from a variety of sources is reproduced.

Alkanone—ketone with two aliphatic groups.

Fatty ketone—a ketone with aliphatic groups one or both of which is from an alkyl or alkenyl group of the type typically found in fatty acids.

Aryl fatty ketone—a ketone with one aryl and one alkyl or alkenyl group and, more particularly and alkyl or alkenyl group of the type generally found in fatty acids.

Phenone—generic phenyl alkyl ketones.

n-π* transition—a photophysical term describing an electronic transition caused by the absorption of light of a specific wavelength; transition involves, in the context used here, the carbonyl group.

π-π* transition—a photophysical term describing an electronic transition caused by the absorption of light of a specific wavelength; transition involves any unsaturated function.

UV-A—light of wavelengths 320-400 nm.

UV-B—light of 270-320 nm.

UV-C—light of shorter wavelengths than 270 nm.

Norrish Type II Reaction—Term that refers to the photochemically induced split of a ketone or ester into two smaller parts one of which is an unsaturated hydrocarbon. Examples of the synthetic use of certain Norrish Type II reactions can be found Kellogg, R. M.; Prins, W. L.; Schoustra, B. M.; Neckers, D.C. Developmental Photochemistry. The Norrish Type II Reaction. *J. Org. Chem.* 1971, 36, 1838-184.

Aryl—includes phenyl groups that may be unsubstituted, mono-, di-, and tri-substituted, $C_6H_{5-n}R_n$ where $R_n=R_1, R_2, R_3, R_4, R_5$ which are the same or different. $R_n$ may be H, linear or branched alkyl $[C_mH_{2m+1}$ where m=1-25], alkenyl $[C_mH_{2m-1}$ where m=1-25] cycloalkyl $[C_mH_{2m-1}$ where m=1-25], alkynyl $[C_mH_{2m-3}$ where m=1-25], mono, di, or poly substituted naphthyl $C_{10}H_{8-n}R_n$, mono, di, or poly substituted anthryl $C_{14}H_{10-n}R_n$, mono, di or poly substituted phenanthryl $C_{14}H_{10-n}R_n$, polycondensed aromatic, $C_{16}H_{10}R_n$ and the like; $R_n$ may also be hydroxy, ether [O—$R_6$ where $R_6$ is linear or branched alkyl $[C_mH_{2m+1}$ where m=1-25], alkenyl $[C_mH_{2m-1}$ where m=1-25], cycloalkyl $[C_mH_{2m-1}$ where m=1-25], alkynyl $[C_mH_{2m-3}$ where m=1-25], mono-, di-, and tri-substituted, $C_6H_{5-n}R_n$, mono, di, or poly substituted naphthyl $C_{10}H_{8-n}R_n$, mono, di, or poly substituted anthryl $C_{14}H_{10-n}R_n$, mono, di or poly substituted phenanthryl $C_{14}H_{10-n}R_n$, polycondensed aromatic, $C_{16}H_{10}R_n$ and the like, F, Cl, Br, I, $C_mH_{2m+2-x}M_x$ where M=F, Cl, Br, I, and x=1-25, thiophenol, thioether [S—$R_6$ where $R_6$ is linear or branched alkyl $[C_mH_{2m+1}$ where m=1-25], cycloalkyl $[C_mH_{2m-1}$ where m=1-25] alkenyl $[C_mH_{2m-1}$ where m=1-25], cycloalkyl $[C_mH_{2m-1}$ where m=1-25] alkynyl $[C_mH_{2m-3}$ where m=1-25], mono-, di-, and tri-substituted, $C_6H_{5-n}R_n$, mono, di, or poly substituted naphthyl $C_{10}H_{8-n}R_n$, mono, di, or poly substituted anthryl $C_{14}H_{10-n}R_n$, mono, di or poly substituted phenanthryl $C_{14}H_{10-n}R_n$, polycondensed aromatic, $C_{16}H_{10}R_n$ and the like, amino [$NR_7R_8$ where $R_7$ and $R_8$ are the same or different and are H or linear or branched alkyl $[C_mH_{2m+1}$ where m=1-25], cycloalkyl $[C_mH_{2m-1}$ where m=1-25] alkenyl $[C_mH_{2m-1}$ where m=1-25], alkynyl $[C_mH_{2m-3}$ where m=1-25], mono-, di-, and tri-substituted, $C_6H_{5-n}R_n$, mono, di, or poly substituted naphthyl $C_{10}H_{8-n}R_n$, mono, di, or poly substituted anthryl $C_{14}H_{10-n}R_n$, mono, di or poly substituted phenanthryl $C_{14}H_{10-n}R_n$, polycondensed aromatic, $C_{16}H_{10-n}R_n$ and the like, piperidino, morpholino, pyrryl, ammonium, $[NR_4^+]$, amido [—$NR_2C$(=O)—], ester, [—$COOR_n$], sulfonamide [—$SONR_2$], aldehyde —[CHO], ketone [—C(=O)R] one or more heterocyclic groups that may or may not be alkylated including thiophene, furan, indole, benzo[b]thiophene, benzo[c]thiophene, benzo[b]furan, benzo[c]furan, indole, heterocyclic groups with two or more heteroatoms, and the like. The group might also consist of substituent(s) (C1-C10)alkyl, acryloxy, methacryloxy, chloro and fluoro. $R_n$ may also be polymeric including poly(ethylene), poly(isopropenyl), poly(propylene), poly(butadienyl), poly(styryl), poly(acylate), poly(methacrylate), poly(fluorocarbon), poly(chlorocarbon) and the like.

Natural oil—Any oil derived from a naturally grown crop particularly peanut, soybean, corn, sunflower, tung, canolla, cotton, coconut, so called vegetable oils, and the like.

BACKGROUND OF THE INVENTION

1. Field of the Invention

The present invention involves a method that uses radiation and particularly solar energy or UV (photochemical) induced processes to convert derivatives of vegetable oils to useful products. In one embodiment, the invention provides a process for converting fatty acid esters or their derivatives to hydrocarbons such as alkenes, dienes, trienes and the like. In a more particular embodiment the invention relates to photochemical methods that convert long chain fatty acids to olefins, dienes and trienes that can, if necessary, be further refined, cracked, reformed or converted to vinyl monomers, halogenated hydrocarbons and other commercial products. In a still more particular embodiment, a method is provided for forming ketones (e.g., fatty ketones) and converting them to olefins by exposing them to radiation.

2. Background

Fossil fuels, specifically products refined from petroleum, remain the principal source of hydrocarbon feed stocks. In addition to being used as a source of gasoline and other fuels, said hydrocarbons are also converted, or used directly, to form the starting materials from whence most synthetically made plastics and commercial solvents are obtained. Thus critical monomers such as styrene, butadiene, acrylic acid, propylene, ethylene and tetrafluoroethylene are currently obtained as either direct cracking products of crude oil or derived from direct cracking products of crude oil. Critical solvents like naphtha, hexanes, petroleum ether, methylene chloride, chloroform, carbon tetrachloride and the like, also are all either directly obtained, or produced, from petroleum. As the supply of fossil fuels, particularly crude oil, dwindles, and as other nations in the world compete for the products derived from oil the costs of raw materials for commercial plastics will increase, supplies will become harder to get and fossil fuel sources will be unable to meet demand.

A series of reports document that a shortage of petroleum products as derived from fossil fuels is anticipated. (Nathan Lewis, Chemical Challenges in Renewable Energy, Cal Tech publication, 2004 incorporated, by this citation, herein). In anticipation of the expected shortages new sources of energy are continually being evaluated and proposed. This application focuses on another facet of the problem, namely, that new sources of raw hydrocarbon feedstocks alternative to petroleum must be developed. Though land is unlikely to have the potential of meeting the needs of the global energy demand through the production of biofuels because the area that would need to be cultivated for such purposes is nearly equivalent to the area now under cultivation world-wide, and biomass conversion to power isn't that efficient anyway (see Lewis, op cit), the use of biomass to produce the raw materials from whence plastics are derived is a much less imposing challenge, and obviously within reach of experimental developments in the chemical sciences using the sun.

A relatively few molecules produced by thermal decomposition (cracking) products of petroleum, unsaturated hydrocarbons mostly, form the basis of most of the commercial plastics industry. These include: ethylene ($CH_2=CH_2$), propylene ($CH_3CH=CH_2$), styrene ($C_6H_5CH=CH_2$) and butadiene ($CH_2=CH-CH=CH_2$). Of these propylene is a particularly important starting material because it is used to form acrylic acid, the base stock of acrylates. Hydrocarbon solvents like petroleum ethers can be used directly from refined petroleum while halocarbon solvents like carbon tetrachloride ($CCl_4$) and perchloroethylene ($C_2Cl_4$) are produced by halogenation of methane and ethylene respectively.

In a recent report (Aug. 22, 2005, Energy Futures: Trends, Outlook and Implications) Don McConnell, CEO Batelle Lab Operations said "Bio-based chemicals can provide a hedge to offset petroleum based polymers & "Bio-refineries" will first be developed from food processing capacity". In accordance with one embodiment of this invention, the oils of common vegetable crops are an alternative potential source of critical monomers such as propylene, ethylene, butadiene, styrene and acrylic acid. Though none have been developed or exploited for same, certain vegetable crops contain percentages of oil ranging from a few percent for corn to almost 30% for crops like peanuts, and these oils, following chemical and photochemical change, are a source of hydrocarbon feed stocks. Major constituents of these oils are derived from glycerol ($CH_2OHCHOHCH_2OH$) in the form of long chain alkyl and alkenyl esters called glycerides. These are likely formed in nature, as they would be in the lab, by an esterification reaction involving reaction of a long alkyl or alkenyl chain carboxylic acid with glycerol. Said long chain fatty acids which include palmitic, stearic, oleic, linolenic and linoleic (and all of the acids derived from food oils—Table 12-2, C. R. Noller, Organic Chemistry, Saunders, 1965, page 209) are themselves, just one step removed from the raw materials of petroleum.

It has long been known that the oils and fats can be removed from the vegetable by extraction with hydrocarbon solvents such as hexanes or petroleum ether, processed and converted to products that can be used in foods such as cooking oils, tofu and the like. However most grower's organizations, for example the soybean growers association, corn growers association, peanut growers association, etc. clearly recognize they could find additional uses of their crops in the industrial market and have efforts that are more or less active to develop alternative (sic industrial, as opposed to food) uses of their crops. Among the largest potential of these is the formation from soya oil of a fuel known as Biodiesel. Biodiesel is defined as mono-alkyl esters of long chain fatty acids derived from vegetable oils or animal fats that conform to ASTM D6751 specifications for use in diesel engines. These mono-alkyl esters are mostly methyl esters that are made from the glycerides by trans-esterification—the process of cooking the glycerides in the presence of a catalyst with an excess of a low molecular weight alcohol, for example methyl alcohol. This produces glycerol as a side product which must be separated. Biodiesel refers to the pure fuel before blending with diesel fuel. Biodiesel blends are denoted as, "BXX" with "XX" representing the percentage of biodiesel contained in the blend (ie: B20 is 20% biodiesel, 80% petroleum diesel). In 2004, approximately 20 million gallons of biodiesel was produced by a group of processors. This is far from capacity and expected to grow. Biodiesel is made entirely from soy and its chemical composition is said to be in the form of the methyl esters of soy: (Source: National Biodiesel Board).

The essential fatty acids that are converted to methyl esters in the formation of Biodiesel are mainly the acids palmitic, stearic, oleic, linoleic and linolenic which are, in turn, the principle fatty acids found in most foodstuffs. Palmitic and stearic acid are the so-called "saturated acids" in that they are comprised of long hydrocarbon chains of 15 and 17 carbons containing no double bonds. Saturated fatty acid esters are disadvantageous in foods so a number of growers organizations have attempted to reduce their content in commercially grown crops either by genetically engineering seeds to produce lower amounts of saturated oils, or by finding growing regions that already produce lower amounts of saturated oils and increasing production in these areas. Oleic, linoleic and linolenic acid, as well as others, are unsaturated acids and therefore preferred in foods with oleic acid being particularly preferred. Typically, in the oil of soy, saturated acids make up from 10 to 20% of the mono, di- and tri-glyceride content while the remainder is a combination of 3 or more unsaturated acid glycerides.

The average molecular weight of soybean oil methyl esters is 292.2. This was calculated using the average fatty acid distribution for soybean methyl esters below.

| Typical Soybean Oil Methyl Ester Profile | | | |
|---|---|---|---|
| Fatty Acid | Percent | Wt. | Formula |
| Palmitic | 12.0 | 270.46 | $C_{15}H_{31}CO_2CH_3$ |
| Stearic | 5.0 | 298.52 | $C_{17}H_{35}CO_2CH_3$ |
| Oleic | 25.0 | 296.50 | $C_{17}H_{33}CO_2CH_3$ |
| Linoleic | 52.0 | 294.48 | $CH_3(CH_2)_4CH=CHCH_2CH=CH(CH_2)_7CO_2CH_3$ |
| Linolenic | 6.0 | 292.46 | $CH_3(CH_2CH=CH)_3(CH_2)_7CO_2CH_3$ |

Fatty acids themselves may be converted by chemical reaction to polymerizable monomers. An oxidized form of soya oil, so-called epoxidized soya oil, is used as an additive in monomer mixtures from whence plastic coatings are made and formed. Polyesters are also derived from dicarboxylic acids such as those that might be obtained from fatty acid feedstocks.

SUMMARY OF THE INVENTION

In accordance with one embodiment of the invention a process is provided that comprises converting fatty acids to the raw materials of plastics that would otherwise come from petroleum. In accordance with a further embodiment of the invention, the converting step includes radiating with sunlight or other artificial sources of light, for example, lamps. In further embodiments, the photodegradation products produced by such solar and photochemical processes are refined, cracked to smaller molecular parts, reformed to more useful and somewhat larger low molecular weight products, oxidized, and eventually converted to many of the low molecular weight monomeric unsaturated hydrocarbons (such as styrene, ethylene, propylene, butadiene and the like) or derivatives such as acrylic acid from whence acrylates can be formed and/or halogenated to form haloethylenes such as vinyl chloride, vinyl bromide, vinyl fluoride, vinylidine chloride, vinylidine fluoride, tetrafluoroethylene, and the like.

A variety of ketones, esters and other derivatives of carboxylic acids can be cracked by light from the sun or artificial sources to lower molecular weight products. In particular organic compounds including ketones and esters undergo a cracking reaction that is known is in the art as the Norrish Type II reaction (see the Appendix) from whence the products are a lower molecular weight ketone (in the case of ketones), or an aldehyde (in the case of esters) and, in both cases, lower molecular weight hydrocarbons specifically alkenes, dienes, trienes and the like. In accordance with one embodiment of the invention, these reactions are used in the solar cracking of fatty ketones to hydrocarbons. In accordance with one embodiment, vegetable oil conversion products are used as starting materials (without additional processing) by one or more subsequent secondary activation step(s), photochemical degradation. Carboxylic acids are easily converted to ketones as well as to esters and many different references teach the synthetic steps to achieve such conversions. In particular, in one embodiment, fatty acids are converted to fatty ketones by Friedel-Crafts reactions from fatty acid chlorides or anhydrides and the products of said conversions are photodegraded.

For example, it is known that the aromatic ketone, valerophenone ($C_6H_5C(=O)CH_2CH_2CH_2CH_3$) made from benzene and valeric acid as the chloride is cracked with light to acetophenone $C_6H_5C(=O)CH_3$ and propylene $CH_3CH=CH_2$, while the analogous hexanophenone ($C_6H_5C(=O)CH_2CH_2CH_2CH_2CH_3$), is cracked with light to acetophenone $C_6H_5C(=O)CH_3$ and 1-butene $CH_3CH_2CH=CH_2$, and heptanophenone $C_6H_5C(=O)CH_2CH_2CH_2CH_2CH_2CH_3$ to acetophenone $C_6H_5C(=O)CH_3$ and 1-pentene $CH_3CH_2CH_2CH=CH_2$. The yields of these reactions are nearly quantitative; that is, one mole of valerophenone produces almost exactly one mole of propylene and one mole of acetophenone. The reactions are photochemically efficient as well with the moles of product produced per photon approaching 1.0 in the best instances. The reaction, as previously indicated, is known in the art as the Norrish Type II reaction discovered in the 30's by R. G. W. Norrish and his students and further studied in the 60's and 70's by George S. Hammond and his students. There are many reviews such as that in Advances in Photochemistry, Volume 5 and in the various textbooks in photochemistry including Turro, N.J. Molecular Photochemistry Mill Valley, Calif. 1991 and Gilbert, A; Baggott, J. Essentials of Molecular Photochemistry, CRC Press 1984.

In accordance with one embodiment of the invention, palmitophenone (phenyl hexadecanone) is photochemically cracked to acetophenone, and 1-tetradecene and stearophenone is photocracked to acetophenone and 1-hexadecene. In a further embodiment, these starting materials are derived from natural oils.

In accordance with one embodiment of the invention, natural oils such as so-called vegetable oils such as soy, corn, peanut, sunflower, coconut and the like can, are hydrolyzed and then further derivatized (e.g., by Friedel-Crafts reactions or other processes) to form photoreactive species such as ketones or esters that can be photochemically degraded (e.g., by the Norrish Type II reaction) with sunlight or other radiation. In one example, this reaction yields acetophenones (or their analogs) and hydrocarbons.

In accordance with a further embodiment, fatty acid alkanones and aliphatic ketones can also be formed from naturally derived fatty acids or their derivatives, and also photochemically cracked by the Norrish Type II reaction with radiation to alkenes and lower molecular weight ketones. In accordance with yet another embodiment the methyl esters of biodiesel are exposed to radiation with short wavelength light directly or after the esters are first converted to light absorbing functions such as the aryl groups. Synthesis of alkanones from fatty acids is well known in the art.

In accordance with a further embodiment the degradation products (e.g., the Norrish II products), the olefins are treated, distilled, refined and the like, such that they can be used to form the raw materials for commercial and industrial plastic formation.

In accordance with one embodiment, the esters of fatty acids such as those derived from vegetable fats and oils by transesterification with alcohols can be expected to decompose by a Norrish Type II process when exposed to short wavelength UV radiation. It is expected that esters containing aromatic groups will react at longer wavelengths of light than those in which the alcohol used in the trans-esterification reaction is an alkanol. In accordance with one embodiment the methyl esters of biodiesel are exposed to radiation with short wavelength light directly.

In accordance with one embodiment, the alkenes, dienes, trienes and the like derived from the Norrish Type II processes (above) are refined, distilled and cracked much as the alkenes, dienes, trienes and the like derived from crude oil are refined, distilled and cracked.

In accordance with one embodiment, the alkenes, dienes, trienes and the like derived from the Norrish Type II processes (above) are selectively oxidized such that acrylic acid is the eventual product. The subsequent reactions of photochemically produced terminal olefins with anhydrous hydroperoxides in the presence of certain organometallic catalysts forming allylic hydroperoxides which can be subsequently cracked to acrylic acid is one such reaction and, as such, is described in Yu, J-Q.; Corey, E. J. *Org. Letters* 2002, 4 2727; Crich, D; Zou, Y; *Org. Letters* 2004, 6, 775; Catino, A. J.; Forslund, R. E.; Doyle, M. P. *J. Amer. Chem. Soc.* 2004, 126, 13622. There are others some of which are appended.

DETAILED DESCRIPTION

One embodiment of the invention is a process comprising hydrolyzing vegetable oil glycerides to fatty acids or fatty acid esters, converting the fatty acid or ester to a light-sensitive compound such as a ketone, and exposing the light-sensitive derivative to radiation to form a hydrocarbon such as an olefin. In a particular embodiment, the fatty acid or ester is converted to an anhydride or acid chloride that is reacted with an aromatic compound in a Friedel-Crafts reaction to produce an aryl alkyl ketone that is photoreactive. To convert the ketone to the desired hydrocarbon products, the Norrish Type II reaction is used. In a particular embodiment, this takes the form of activating them to the phenones or to derivatives such as aromatic esters that are susceptible to UV-A and UV-B wavelengths.

Conversion to an aromatic ketone (e.g., phenone) can be accomplished in a number of ways but most generally takes advantage of an electrophilic substitution reaction such as that referred to as a "Friedel-Crafts" reaction. In a common example of the Friedel Crafts reaction, an aromatic hydrocarbon such as benzene or toluene is added to a slurry of a 2:1 mixture of the carboxylic acid derivative (anhydride or acid chloride) and anhydrous aluminum chloride in a non-reactive solvent such as methylene chloride or carbon disulfide and a molar equivalent of the aromatic hydrocarbon is added and the mixture refluxed for a period. Subsequently the reaction mixture is poured into ice, extracted with hydrocarbon solvent and the subsequently formed solution neutralized by washing with base, dried and the solvent distilled. The residue is the aromatic ketone or phenone.

This process is just one of the many ways in which a fatty acid or its derivative can be converted in one step to an aryl alkyl ketone. The reaction has been described in numerous reviews including that by Price, C. C. in Adams, R. *Organic Reactions* Vol III., John Wiley and Sons, New York, N.Y., 1946 P. 1, and that by Berliner, E.; *Organic Reactions* Vol. V, John Wiley and Sons, New York, N.Y., 1949 P. 229; as well as later series Friedel-Crafts and Related Reactions, George A. Olah, Interscience Publishers, 1964 and that by Patai, The Chemistry of the Carbonyl Group, Saul Patai, Editor, Interscience Publishers 1966. Details of specific preparations can be found in Allen and Barker, Organic Synthesis, Coll Vol II, 1943 156 and in Wagner, R. B.; Zook, H. B.; Synthetic Organic Chemistry, pp 316 ff, John Wiley & Sons, 1953. The specific preparation of stearophenone can be found in Seidel and Engelfried, *Ber.* 1936, 69B, 2578. Unsaturated ketones as would anticipated from oleic acid, linoleic acid and linolenic acid can also be achieved by this route as found in Darzens, *Compte. Rendu* 1940, 211 435. It will be recognized that any of the fatty acids generated by the hydrolysis of typical vegetable oils will be susceptible, when converted to an acid anhydride or acid chloride, to Friedel Crafts reaction conditions and it is our intention to cover all such cases. Such reactions have been reported with ferrocene [Synthesis and redox properties of ferrocene derivatives containing an oleyl group. Butkus, Eugenius; Tauraite, Daiva; Barauskas, Justas; Talalkyle, Zita; Razumas, Valdemaras. Journal of Chemical Research, Synopses (1998), (11), 722-723.] and with styrene Ralston, Anderson W.; Vander Wal, Robert J. Acyl styrenes. (1940), U.S. Pat. No. 2,197,709 as well as with linoleyl and linolenoyl chloride Ralston, A. W.; Vander Wal, R. J.; Bauer, S. T.; Segebrecht, E. W. Fatty-acyl-modified resins-dicyclopentadiene, coumarone and indene types. Journal of Industrial and Engineering Chemistry (Washington, D.C.) (1940), 32 99-101.

Many modifications of Friedel Crafts acylation reaction conditions are known. As specific procedure, that used for the synthesis of a simple aryl alkyl ketone is illustrated below.

A mixture of 0.11 m [11.5 g] styrene, 0.11 m[15 g] $AlCl_3$ and 75 ml chlorobenzene was prepared and 30 g oleyl chloride added. The reaction was stirred and heated to 40° for one hour and then poured onto ice. Linoleyl styrene, linolenyl styrene and lauroyl styrene were prepared similarly.

Other synthetic processes may also prove beneficial in the synthesis of ketones. One such is that reported oxidative rearrangements of arylalkenes with [hydroxy(tosyloxy)iodo] benzene in 95% methanol: a general, regiospecific synthesis of a-aryl ketones. Justik, M. W.; Koser, G. F. *Tetrahedron Letters* 2004, 45, 6159-6163. Other methods of adding photoreactive moities to fatty acid derivatives that may be used in other embodiments of the invention include those disclosed in *J. Med. Chem.* 1988, 31, 1052. and WO 2005 0553702.

Friedel Crafts reactions involving unsaturated acids and acid chlorides/anhydrides such as oleic acid and its derivatives, linoleic acid and its derivatives and linolenic acid and its derivatives may produce side products. A method to avoid this is to require a hydrogenation step in order to make the reaction more efficient subsequently. Thus unsaturates are removed prior to the next acylation step which produces the ketones. This has the effect of converting each of the unsaturated fatty acids to stearic acid which is subsequently converted to the ketone.

In accordance with a further embodiment, fatty acid alkanones, aliphatic ketones can also formed from fatty acids or their derivatives, and also photochemically cracked by the Norrish Type II reaction with light to alkenes and lower molecular weight ketones. Synthesis of alkanones from acids is well known in the art. For example dehydration of the octadecanoic acid to the form the ketene and/or dehydrochlorination of the acid chloride followed by ketene dimerization has been reported (U.S. Pat. No. 2,369,919 Sauer, J. C "Ketoethenones and Process Therefor") to form octadecanoylhesadecylethenone $C_{17}H_{33}COC(C_{16}H_{33})=C=O$ in high yield. However there are a number of other simple routes to alkyl fatty ketones. The decarboylation of fatty acids over thoria at high temperatures (400-500°) produces the symmetrical alkanone in near quantitative yield. Thus octanoic acid, on decarboxylation produces 8-pentadecanone. Higher molecular weight ketones can be synthesized using the same procedure from the methyl esters. For instance di-n-undecylketone is prepared in 93% yield from lauric acid (Swann, Appel and Kistler, *Ind. Eng. Chem.* 1934, 26, 1014) and stearone (di-n-heptadecyl ketone) in 95% from stearic acid (Curtis, Dobson and Hatt, *J. Soc. Chem. Ind. London* 1947, 66, 402). Unsaturated acid esters, for example, 9-undecenoic acid, ethyl ester give 80-90% yields of the ketone (undecylenone). It is thus expected that oleic acid, linoleic acid and linolenic acid will dimerize under similar conditions to the appropriate ketone. The subsequent photoreactions of consequence are discussed in detail in the various textbooks in photochemistry including Turro, N.J. Molecular Photochemistry Mill Valley, Calif. 1991 and Gilbert, A; Baggott, J. Essentials of Molecular Photochemistry, CRC Press 1984. In accordance with a further embodiment the degradation products, the olefins are treated, distilled, refined and the like, such that they can be used to form the raw materials for commercial and industrial plastic formation.

Photochemical Reaction:

It will be recognized that there are numerous alternative possibilities for carrying out synthetic scale photochemical processes (eg. Neckers, D.C. Continuous Oxidation Method. U.S. Pat. No. 4,849,076, Jul. 18, 1989). The examples herein are cited to illustrate the principle only. It will also be recognized that optimization of these processes is possible such that all of the acetophenone or analogous aromatic ketone product is removed at the instant of formation. This expedient is particularly useful. Many aromatic ketones are, themselves, commercially useful as outlined in Appendix 2. It must also be recognized by those familiar with the art that the ketone and other carbonyl group containing products are themselves photoreactive and could be, as such, be further converted to aromatic alcohols and other compounds containing specific functional groups in situ. Such subsequent reaction processes are also within the scope of this invention.

We include, as evidence of this recognition, a list of aromatic ketones that when incorporated (via Friedel Crafts or activating steps) into crop fatty acids may confer Norrish Type II reactivity when irradiated with UV-A and UV-B light. These ketones include those prepared by Friedel Crafts reactions of benzene, toluene, o-, m- and p-xylene, ethyl benzene, o-methyl ethyl benzene, m-methyl ethyl benzene, p-methyl ethyl benzene, n-propylbenzene, o-methyl n-propyl benzene, m-methyl n-propyl benzene, p-methyl n-propyl benzene, isopropylbenzene, o-methyl isopropyl benzene, m-methyl isopropyl benzene, p-methyl isopropyl benzene, t-butyl benzene, o-. m- and p-methyl tert-butylbenzene, o-. m- and p-ethyl tert-butyl benzene, o-. m- and p-n-propyl tert-butyl benzene, o-. m- and p-isopropyl tert-butyl benzene, o-. m- and p-n-butyl tert-butyl benzene, o-. m- and p-sec-butyl tert-butyl benzene, o-. m- and p-isobutyl tert-butyl benzene, m-di-tert-butylbenzene. p-di-tert-butylbenzene, 1,3,5-tri-tert-butyl-benzene, and all other appropriately substituted alkylbenzenes of 20 or less carbon atoms in the alkyl chain. The list of reactive ketones that can be prepared by Friedel Crafts reactions also includes all ketones prepared from anisole and methyl, ethyl, n-propyl, isopropyl, n-butyl, isobutyl, sec-butyl, tert-butylbenzene substituted with a single o-methoxy, m-methoxy and p-methoxy group. Compounds with 2, 3, 4 or 5 methoxy functions are also included. Also included a similarly substituted ethoxy, n-propoxy, isoproxy, n-butoxy, isobutoxy, sec-butoxy, tert-butoxy, as well as any alkoxylated benzene of up to 10 carbon atoms, as a saturated linear or branched alkyl group, an alkenyl or alkynyl function similar in composition. As in the instance of methoxy, multiple alkoxy functions on the benzene ring are also included as is benzyloxy and other aryloxy functionalities. It is also anticipated that ketones made from the o-, m-, p-phthalic acids should be useful in the invention. All other substituted aromatic ketones the ketone function of which is known to be reactive in typical n-$\pi$* photoreduction sequences are included as part of this further embodiment. Typical of these, though not exclusively, is the list of ketones that can be reduced to pinacols found in Table 7-3 of Neckers, D.C. *Mechanistic Organic Photochemistry*, Reinhold, N.Y., 1967. Halogenated aryl fatty ketones are also possible reactants but, as is well known in the art, these cannot be synthesized by Friedel Crafts reaction chemistry.

Irradiation of Phenones

Example 1

In a typical procedure, palmitophenone [$C_6H_5C(=O)C_{16}H_{33}$] was irradiated in hexane with a 300 nm artificial light source (UV lamp—Rayonet 350 nm see table) for a few hours. The gas chromatogram of the reaction mixture shows mainly two products—acetophenone and 1-tetradecene [$CH_2=CH(CH_2)_{11}CH_3$] as well as some recovered starting material and a small amount of side product. The specific procedure, along with the data, is reproduced below.

Example 2

After a few hours irradiation of stearophenone [$C_6H_5C(=O)C_{18}H_{37}$] in hexane at 300 nm, the products are acetophenone and 1-hexadecene ($CH_2=CH(CH_2)_{13}CH_3$. The reactions are almost quantitative in that nearly 80% of the reacting phenone is converted to olefin.

The reactions illustrated above rely upon the Norrish II reaction of the aryl alkyl ketone derivative of the fatty acids. In accordance with another embodiment of the invention, alkyl fatty ketones can be photodegraded to produce olefins.

Example 3

2-Hexadecanone is the methyl ketone derived from palmitic acid. When irradiated at 300 nm in a Rayonet reactor for 7 hours 1-tetradecene and acetone were formed. In contrast to the reaction with the phenones, the reaction with methyl hexadeca-2-one produced a higher yield of side product. This is indicated in the below Table *Chemical Yields of Norrish Type II Products*.

It is an embodiment that fatty acid esters can be photodegraded to produce olefins by the Norrish II reaction. It is well known in the art that though esters behave similarly to ketones when they are irradiated with light, though the essential process for light absorption in esters demands a much shorter wavelength of light. In theory the ester function is more electronically stable than the ketone function, and hence the former requires more energy for it to be promoted to its excited state. The n-$\pi$* transition of esters occurs around 230 nm if the ester is entirely aliphatic (as are all of the esters in methyl soy) while the n-$\pi$* transition in phenones occurs around 320 nm in the normal, unsubstituted case and the n-$\pi$* transition in alkanones occurs at 290 nm in the normal case.

Example 4

Irradiation of methyl palmitate. Methyl palmitate was dissolved in a small amount of hexane and irradiated in a quartz container (UV cuvette) at 253.7 nm in the Rayonet reactor. After 7 hours a small amount of 1-tetradecene was formed. After 24 hours a larger amount of 1-tetradecene and a corresponding isomer (to be identified but likely 2-tetradecene ($CH_3CH=CHCH_2(CH_2)_9CH_3$) was obtained.
Chemical Yields of Norrish Type II Products—
  from 2-hexadecanone p $CH_3-(CH_2)_{13}-COCH_3$ (in $C_6H_6$: $\lambda_{max}=284$, $\epsilon_{284}=22$, $\epsilon_{300}=14$)] irradiated at 300 nm for 7 hours, 47.3% 1-tridecene, 2.1% 1-methyl-2-undecylcyclobutanol;
  from hexadecanophenone[$CH_3-(CH_2)_{14}-COC_6H_5$ (in $C_6H_6$: $\lambda_{max}=322$, $\epsilon_{322}=56$, $\epsilon_{300}=57$) irradiated at 350 nm for 7 hours 53.7% 1-tetradecene, 9.3% acetophenone and 3. 3% 1-phenyl-2-tridecylcyclobutanol,
  from octadecanophenone $CH_3-[(CH_2)_{16}-COC_6H_5$ (in $C_6H_6$: $\lambda_{max}=322$, $\epsilon_{322}=58$, $\epsilon_{300}=61$)] irradiated at 350 nm 71.8% 1-hexadecene, 5.7 acetophenone and 3.3% 1-phenyl-2-pentadecylcyclobutanol
  from methyl palmitate irradiated at 254 nm for 48 hours 20.2% 1-tetradecene and 2% 2-tetradecene.

It is also recognized by those familiar with the art that the aromatic residue ($C_6H_5$ is the example cited in examples 1 and 2) may be one of a number. It should also be recognized, that n-$\pi$* configuration of the excited state formed by the ketone or the ester provides for high reactivity. It should also be recognized by those familiar with the field that certain ketones may not be highly reactive in the photoprocesses anticipated because of the so-called effect of ortho substituted hydrogen donors. Such common functions as ortho-methyl and ortho-hydroxy are included in this group in aromatic ketones containing same are prone to intramolecular hydrogen abstraction from the ortho substituted function that is unproductive. Though functionalities that produce $\pi$-$\pi$* excited states when in a ketone or ester form may not, a priori be excluded, their reactivity is predicted to be substantially less.

The photochemical reactions of fatty acid esters made from alkanols generally require a shorter wavelength light source than do the photochemical reactions of the corresponding alkanones or phenones. However, once the fatty acids are formed by hydrolysis, conversions to esters other than methyl esters would use alcohols other than methanol. In another embodiment of the invention, by forming esters of the fatty acids containing unsaturated or aromatic functions the absorption maximum of the fatty acid function can be shifted to longer wavelengths such that the esterified product demonstrates susceptibility to UV-A and UV-B wavelengths. Such preparations are described as well in Wagner, R. B.; Zook, H. B.; Synthetic Organic Chemistry, pp 479 ff, John Wiley & Sons, 1953. Aromatic esters are another photoreactive species that can be used in accordance with other embodiments of the invention.

Another method involves irradiation of the fatty acid methyl esters with UV-C light. Methyl soy or other essential fatty acid products can be used, in the process directly. However other esters may also be susceptible to UV-A and UV-B wavelengths and such esters are included as being preferable. The photodecomposition of esters can be sensitized by light absorbing species that form excited states having higher energies than those of the esters while being, themselves, unreactive and this mitigates the requirement for short wavelength source somewhat. This is a particular possibility when palmitic, stearic, oleic, linoleic and linolenic esters are prepared from phenols and other such compounds containing aromatic groups. This is because the excited state energies of phenyl esters (both singlet state energies and triplet state energies) as well as those of esters of disubstitued phenols, (o-, m, and p), cresols and the like as palmitates, oleates, stearates, linoleates and linoleneates, lie below those of aliphatic fatty acid esters. Thus it would anticipated that the reaction of phenyl palmitate would produce 1-tetradecene just as the reaction of methyl palmitate does, but do so more quickly and efficiently. And the sensitized reactions of both would be expected to be even faster still. Specific sensitizers that would function in this instance would include all those with singlet state and triplet state energies higher than phenyl palmitate. A table of such energies can be found in any standard book on photochemistry but one that is particularly useful in this context is that by Murov, S. L; Carmichael, I; Hug, G. L *Handbook of Photochemistry* $2^{nd}$ ed. New York, 1993. Though the excited state energy of fatty acid esters such as phenyl palmitate, phenyl stearate, phenyl oleate, phenyl linoleate and phenyl linolenate have not been measured, it can be anticipated that the triplet energies, in all likelihood the reactive state, would be ≈300 kJ/mol. In particular it would be expected that acetophenone or propiophenone might therefore be acceptable photosensitizers as would benzoic acid and a number of its derivatives, benzonitrile and a number of its derivatives, certain phenols, some anilines, benzimidazole, certain pyridines, benzene and a number of substituted benzenes such as those containing fluorine substituents, phenyl acetic acid, phenyl propionoic acid and even methyl acrylate, methyl methyl acrylate as well as polymers derived therefrom, and the like. Of course it is recognized by those familiar with the art that the sensitizer itself should be unreactive under the conditions in which is used for sensitization and thus would be carefully chosen. It should also be recognized that the sensitizer must not react elsewise with the target except as, in the case of phenyl palmitate, it must absorb at more convenient wavelengths than does the acceptor target and must otherwise make the chemical processes faster, cleaner and more convenient than they might otherwise be. In the sensitized reaction of methyl palmitate for instance, a sensitizer absorbing light at longer wavelength than the absorption maximum of methyl palmitate might be expected to transfer the energy therein derived if it were in a solution containing a higher concentration of methyl palmitate than sensitizer. This would have the effect of producing the same excited state derived from methyl palmitate by direct light absorption. It should be recognized that the list of sensitizers above is representative, and not exhaustive. Many other compounds can, and likely will, sensitize the target Norrish Type II decomposition processes. Of course it is implied that what is described for methyl and phenyl palmitate is also implied for esters of stearic, oleic, linoleic and linolenic acids as well as esters from any naturally obtained fatty acid found in soy, corn, sunflower, peanut, coconut, palm, cotton, canola and the like. Norrish Type II reactions are also reported for polymeric esters including ethylene glycol polyterephthalate (Gueris, C.; Meybeck, J.; *Bull. Soc. Chim. France* 1972, 2320) and di-n-butyl terephthalate (Day, M.; Wiles, D. M; *Can. J. Chem.* 1971 49 2916). Accordingly, polymeric esters derived from fatty acids represent additional embodiments of the invention.

Two other practical facts will also be recognized by those familiar with the art. First only artificial light sources will be of sufficiently short wavelength to cause photodegradation of esters. One cannot use sunlight for the direct irradiation at the shorter wavelengths. In the instance of the sensitized process, however, one will be able to use longer wavelength sources. And the solvent systems and containers (if there are any) used when esters are irradiated must be transparent to short wavelength radiation. One cannot use a glass apparatus, for example, nor can one anything but an aliphatic hydrocarbon solvent. In the case of methyl soy, one might consider irradiating biodiesel itself with short wavelength light. Of course it is also recognized by those familiar with the art that the solutions to be irradiated must, themselves, be transparent. It does not work to use crude materials particularly if those crude materials contain dark or off-color impurities. Of course it will also be recognized by those familiar field that the successful experimental profile is derived if one measures the ultraviolet absorption spectrum of the prospective photochemical reactant and tailors the output of the light source used for the irradiation to wavelengths identical, or nearly so, with the absorption maximum of the prospective photoreactant.

It will be recognized by those familiar with the art that there are many points of modification of which the examples are indicative. As the examples illustrate, one can vary the fatty ketone derived from the natural oil as either aromatic or alphatic and one can also vary the functional group. Fatty acid amides such as those prepared from the fatty acid of one of its actived derivatives with ammonia or amines are also photoreactive and undergo Norrish Type II degradations. The amides may be alkyl amides, (Mellier, D.; Pete, J. P.; Portella, C. *Tet. Letters* 1971, 47 4559) benzamides (Coyle, J. D.; Kingston, D. H *Tet. Letters* 1976, 49 4525.) α-oxoamides (Aoyama, H.; Sakamoto, M.; Kuwabara, K.; Yoshida, K.; Omote, Y. *J. Amer. Chem. Soc.* 1983, 105 1958) and nylons (Do, C. H.; Pearce, E. M.; Bulkin, B. J.; Reimschuessel, H. K; *J. Polym Sci, Part A. Polymer Chemistry,* 1987, 25 2301) all of which are susceptible to Norrish Type II processes.

Having described the invention in detail and by reference to specific embodiments thereof, it will be apparent that numerous variations and modifications are possible without departing from the scope of the invention as defined by the following claims.

Appendix 1

Scope of the Norrish Type II Reaction

The photochemical reactions aromatic ketones are known to undergo are summarized below.

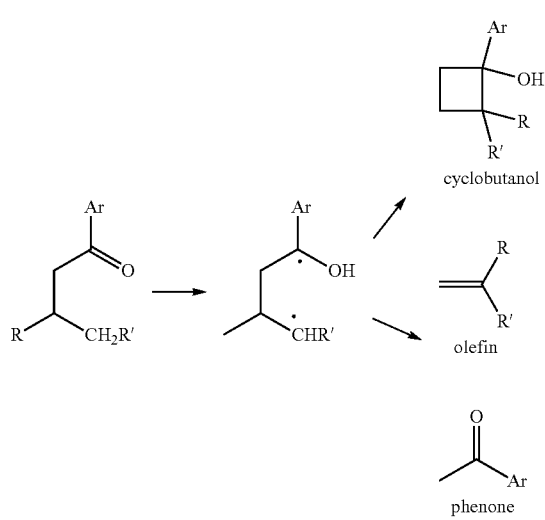

Ar = fatty phenone

The Norrish Type II reaction (lowest above) is a split of the ketone to a lower molecular weight ketone and a terminal olefin having an alkyl chain that is one less than that found in the starting ketone. Thus butyrophenone, from butyric acid (alkyl chain not counting the carbon of the carboxylic acid, C-3) produces ethylene and valerophenone (alkyl chain not counting the carbon of the carboxylic acid, C-4) propylene. The enol tautomerizes to a derivative otherwise known as an acetophenone in the case of phenyl ketones or more generally to an aryl ketone in the case of substituted aromatic ketones. The syntheses of aryl ketones by the procedures described below for the purposes outlined in this specification is also an embodiment of this invention. There are numerous reviews discussing Norrish Type II processes including that by Scaiano, J. C., Accts. Chem. Res., 1982 15, 252.

One skilled in the art will recognize that the number of carbon atoms in the alkyl function must be sufficient so that they can be branched and that the number of carbons in the alkenyl function should be sufficient so that they can accommodate a double bond.

One skilled in the art will also recognize that though the specification above identifies alkenes with just one double bond, that 2, 3, 4 or more double bonds might also be part of the alkenyl chain and that each additional double bond reduces the counted number of hydrogen atoms by 2 [$C_mH_{2m-1}$ to $C_mH_{2m-3}$ $C_mH_{2m}-C_mH_{2m-7}$ etc.] though one skilled in the art will also recognize that the larger the number of double bonds becomes, the more inherently unstable the compound. Likewise, the number of cycloalkyl rings can be greater than the single ring so identified and the number of triple bonds in the linear or branched array greater than 1 as well. In the latter case one might anticipate [$C_mH_{2m-3}$, $C_mH_{2m-5}$, $C_mH_{2m-7}$ etc.].

It also is anticipated that one skilled in the art would recognize that $R_n$ could be polymeric as in the case of poly(styrene), poly(ethylene), poly(tetrafluoroethylene) etc.

The alkyl group in the photoreactive ketone, above, can be any of the groups cited in 000x save it must contain a minimum of three carbons the third from the ketone or ester function (above) having at least one hydrogen. Thus Aryl-C(=O)$CR_8R_9CR_{10}R_{11}CHR_{12}R_{13}$ in which $R_8$-$R_{13}$ may be any of the alkyl, alkyenyl, alkynyl, cycloalkyl, phenyl, substituted phenyl, aryl and the like cited above with the alkyl group derived from the previously identified fatty acids, palmitic and stearic (also lauric and caprilic) being preferred. Alkenyl functions as in oleic, linoleic and linolenic acid are also preferred.

The groups cited herein are best viewed in the following graphic formulae (Chem 1—general 'phenone' formula, Chem 2—specific palmitophenone and stearophenones, Chem 3—generic alkanone formula) wherein the substituents as cited above are specifically incorporated.

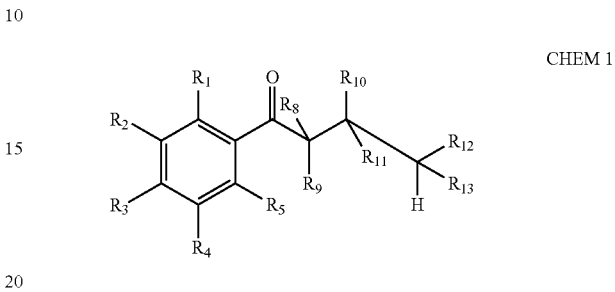

CHEM 1

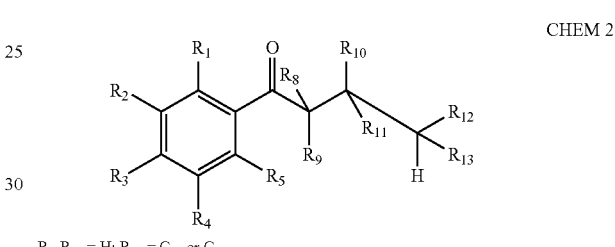

CHEM 2

$R_1$-$R_{12}$ = H: $R_{13}$ = $C_{14}$ or $C_{16}$

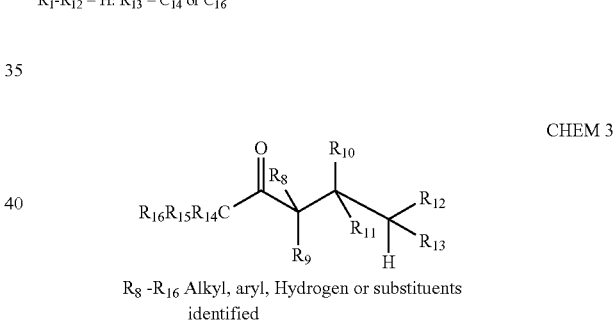

CHEM 3

$R_8$ -$R_{16}$ Alkyl, aryl, Hydrogen or substituents identified

Light suitable for the purpose of Norrish Type II reactions that specifically activates the aryl ketones (so-called phenones in the case where aryl is phenyl) is in the mid-range UV region of the spectrum, the so-called UV A region. This ranges from 300 nm to 400 nm and somewhat beyond into the visible region of the spectrum. The actual wavelengths will depend on the specific functionalized fatty acid derivative and in particular on the aromatic component of the compound being specifically predicted by the absorption spectrum of the ketone or derivative and its excited state (Jablonski) diagram. The Norrish Type II reaction is general and many, many specific possibilities are thereby incorporated herein. Specifically, as in CHEM 1, the light may be absorbed by phenyl and substituted phenyl with these being preferred but also by naphthyl, anthryl, phenanthryl, and substituted naphthyl, anthryl, phenanthryl CHEM 4 with these likely being excluded because the excited states formed therefrom may be non-reactive in the subsequent excited state process. This is clear to those familiar with the art as described in Turro, Modern Molecular Photochemistry, Mill Valley, Calif., 1991.

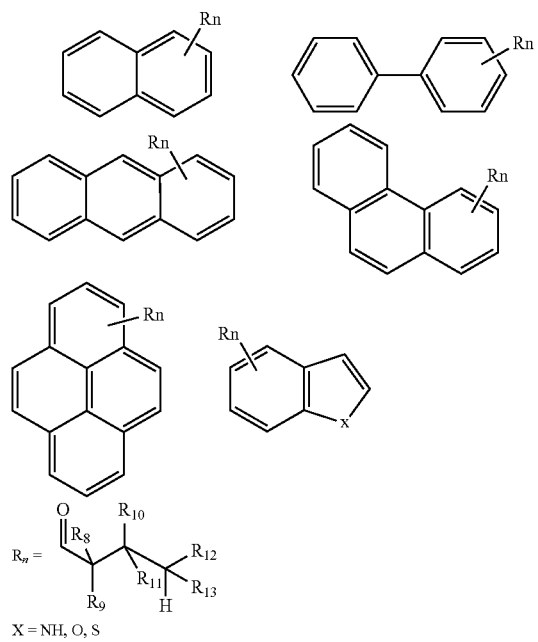

CHEM 4

X = NH, O, S

Light of somewhat shorter wavelength can be used to degrade aliphatic [CR$_{14}$R$_{15}$R$_{16}$C(=O)CR$_{17}$R$_{18}$R$_{19}$] ketones which can also be made from fatty acids by a variety of different methods (Wagner, R. B.; Zook, H. B. *Synthetic Organic Chemistry*, Wiley, New York 1965 and incorporated herein for reference). The essential reaction is shown below for the lowest molecular weight ketone for which the Norrish Type II reaction is a possibility, 2-pentanone. Note the olefin formed by the degradation (not shown) must be ethylene. As above, the alkyl group can be any of the groups cited in 000x and, as in the case of the phenone, it must contain a minimum of three carbons the third from the ketone function having at least one hydrogen.

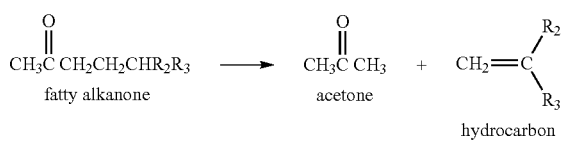

The Norrish Type II reaction follows a similar course with aliphatic ketones (CHEM 3) though the mechanism is somewhat different. Since the light required for the photodegradation of alkanones is also shorter in wavelength it is anticipated that secondary processes including most specifically olefin isomerization might be observed and these are incorporated herein. For example, 2-hexanone CH$_3$C(=O)C$_4$H$_9$ when properly exposed to light produces acetone CH$_3$C(=O)CH$_3$ and propylene (+other products) while 2-heptanone CH$_3$C(=O)C$_5$H$_{11}$ produces 1-butene and acetone+other products. The wavelengths of light needed for these reactions are in the so-called UV-B region with specific wavelengths of maximum absorption used for it ranging from about 275 nm to 300 nm for the typical aliphatic ketone. Aliphatic aldehydes are similarly reactive. Hexanal C$_5$H$_{11}$C(=O)H produces acetaldehyde CH$_3$C(=O)H and 1-butene; heptanal C$_6$H$_{13}$C(=O)H yields acetaldehyde and 1-pentene. It will be widely recognized that the possibilities for the photochemical degradation of aliphatic ketones as well as of aliphatic aldehydes is, similarly, very large. An early review is that by Wagner, P. J. *Acct. Chem. Res.* 1971, 4, 168 incorporated herein for reference.

The ester functionality CHEM 5 differs from the ketone functionality by an additional oxygen atom. Methyl heptanoate, for example, has the chemical structure CH$_3$C(=O)C$_6$H$_{13}$. Esters absorb light at much shorter wavelengths than ketones or aldehydes. The light required to degrade esters is in the deep UV-B region ranging from 220 to 250 nm or thereabouts. The products of the Norrish Type II reaction are the same. Methyl hexanoate (methyl ester of hexanoic acid) produces methyl acetate (CH$_3$C(=O)CH$_3$ and 1-pentene. Methyl heptanoate CH$_3$C(=O)C$_7$H$_{15}$ (methyl ester of heptanoic acid) produces methyl acetate and 1-hexene. These reactions, because they use deep UV radiation, often produce side products and the olefins produced are likely able to isomerize. For example 1-pentene (CH$_2$=CHCH$_2$CH$_2$CH$_3$) may be accompanied by 2-pentene (CH$_3$CH=CHCH$_2$CH$_3$) and 1-hexene CH$_2$=CHCH$_2$CH$_2$CH$_2$CH$_3$ by 2-hexene CH$_3$CH=CHCH$_2$CH$_2$CH$_3$ and 3-hexene CH$_3$CH$_2$CH=CHCH$_2$CH$_3$. But the principle products are the same and these isomerization processes an advantage. For photoreactions of carboxylic acid derivatives, see Coyle, J. D., Chemical Reviews, 1978, 78, 97.

It is widely recognized by those skilled in the art that esters result from reaction of acids (or their deriviatives) with alcohols as in the case of the methanol used to form methyl soy, or phenols as would be the case of the formation of phenyl palmitate, stearate, oleate, linoleate, linolenate and the like. The general ester formula CHEM 4 identifies the functionality. In the case of an alcohol, R$_{14}$-R$_{16}$ are H, alkyl, alkenyl, cycloalkyl or alkynyl as defined above. In the case of an aromatic ester R$_{14}$-R$_{16}$ are the groups commonly identified as aromatic groups in typical organic chemistry textbooks such as Noller, op. cit.

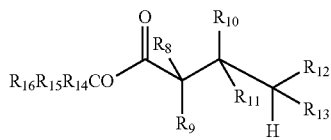

R$_8$-R$_{16}$ Alkyl, aryl, Hydrogen or substituents identified

The reaction as generally identified in the case of esters is shown in CHEM 5.

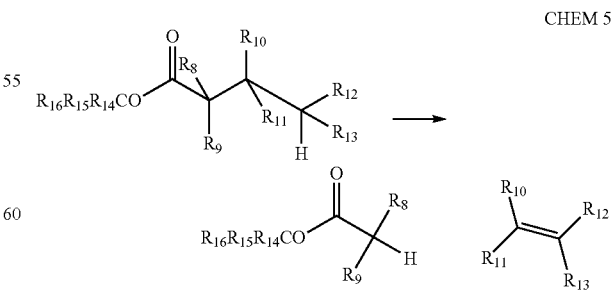

CHEM 5

If one or more of the groups (R$_{14}$-R$_{16}$, CHEM 5) is aromatic, it may be a phenyl that may be unsubstituted, mono-, di-, and tri-substituted phenyl, aryl, C$_6$H$_{5-n}$R$_n$ where R$_n$=R$_1$, $R_2$, $R_3$, $R_4$, $R_5$ which are the same or different. $R_n$ may be H, linear or branched alkyl [$C_mH_{2m+1}$ where m=1-25], alkenyl [$C_mH_{2m-1}$ where m=1-25] cycloalkyl [$C_mH_{2m-1}$ where m=1-25], alkynyl [$C_mH_{2m-3}$ where m=1-25], hydroxy, ether [O—$R_6$ where $R_6$ is linear or branched alkyl [$C_mH_{2m+1}$ where m=1-25], alkenyl [$C_mH_{2m-1}$ where m=1-25], cycloalkyl [$C_mH_{2m-1}$ where m=1-25], alkynyl [$C_mH_{2m-3}$ where m=1-25], thiophenol, thioether [S—$R_6$ where $R_6$ is linear or branched alkyl [$C_mH_{2m+1}$ where m=1-25], cycloalkyl [$C_mH_{2m-1}$ where m=1-25] alkenyl [$C_mH_{2m-1}$ where m=1-25], cycloalkyl [$C_mH_{2m-1}$ where m=1-25] alkynyl [$C_mH_{2m-3}$ where m=1-25], amino [$NR_6R_7$ where $R_6$ and $R_7$ are the same or different and are H or linear or branched alkyl [$C_mH_{2m+1}$ where m=1-25], cycloalkyl [$C_mH_{2m-1}$ where m=1-25] alkenyl [$C_mH_{2m-1}$ where m=1-25], alkynyl [$C_mH_{2m-3}$ where m=1-25], piperidino, morpholino, pyrryl, C1-C6 chloroalkyl, C1-C6 fluoroalkyl, one or more phenyl or benzyl groups optionally substituted, one or more heterocyclic groups that may or may be alkylated including thiophene, furan, indole, benzo[b]thiophene, benzo[c]thiophene, benzo[b]furan, benzo[c]furan, indole, heterocyclic groups with two or more heteroatoms, and the like. The group might also consist of substituent(s) (C1-C4)alkyl, acryloxy, methacryloxy, chloro and fluoro.

One skilled in the art will also recognize that though the specification above identifies alkenes with just one double bond, that 2, 3, 4 or more double bonds might also be part of the alkenyl chain and that each additional double bond reduces the counted number of hydrogen atoms by 2 [$C_mH_{2m-1}$ to $C_mH_{2m-3}$ $C_mH_{2m-}C_mH_{2m-7}$ etc.] though one skilled in the art will also recognize that the larger the number of double bonds becomes, the more inherently unstable the compound. Likewise, the number of cycloalkyl rings can be greater than the single ring so identified and the number of triple bonds in the linear or branched array greater than 1 as well. In the latter case one might anticipate [$C_mH_{2m-3}$, $C_mH_{2m-7}$, $C_mH_{2m-7}$ etc.].

It also is anticipated that one skilled in the art would recognize that $R_n$ could be polymeric as in the case of poly (styrene), poly(ethylene), poly(tetrafluoroethylene) etc.

The alkyl group, above, can be any of the groups cited in 000x save it must contain a minimum of three carbons the third from the ester function (above) having at least one hydrogen. Thus Aryl-C(=O)OC$R_8R_9$C$R_{10}R_{11}$CH$R_{12}R_{13}$ in which $R_8$-$R_{13}$ may be any of the alkyl, alkyenyl, alkynyl, cycloalkyl, phenyl, substituted phenyl, aryl and the like cited above with the alkyl group derived from the previously identified fatty acids, palmitic and stearic (also lauric and caprilic) being preferred. Alkenyl functions as in oleic, linoleic and linolenic acid are also preferred.

It will be widely recognized by those familiar with the art that aromatic esters may be more photoreactive than aliphatic esters in the processes of interest (incorporated reference, Anderson, J. C.; Reese, C. B. *Tet. Lett* 1962, 1-4; subsequent Conrad, P. G. II, Givens, R. S.; Weber, J. F. W.; Kander, K *Org Lett* 2000 2 1545 ff). This is because aromatic esters are more absorbing in the UV-A and UV-B regions of the spectrum. The introduction of an aryl group ($R_{14}$-$R_{16}$=Aryl CHEM 5) is preferred. In particular aryl functions with electron donating groups such as alkoxy, thioalkoxy, amino and the like are preferred.

$R_y$ above is as aryl including phenyl groups that may be unsubstituted, mono-, di-, and tri-substituted, $C_6H_{5-n}R_n$ where $R_n=R_1, R_2, R_3, R_4, R_5$ which are the same or different. $R_n$ may be H, linear or branched alkyl [$C_mH_{2m+1}$ where m=1-25], alkenyl [$C_mH_{2m-1}$ where m=1-25] cycloalkyl [$C_mH_{2m-1}$ where m=1-25], alkynyl [$C_mH_{2m-3}$ where m=1-25], mono, di, or poly substituted naphthyl $C_{10}H_{8-n}R_n$, mono, di, or poly substituted anthryl $C_{14}H_{10-n}R_n$, mono, di or poly substituted phenanthryl $C_{14}H_{10-n}R_n$, polycondensed aromatic, $C_{16}H_{10}R_n$ and the like; $R_n$ may also be hydroxy, ether [O—$R_6$ where $R_6$ is linear or branched alkyl [$C_mH_{2m+1}$ where m=1-25], alkenyl [$C_mH_{2m-1}$ where m=1-25], cycloalkyl [$C_mH_{2m-1}$ where m=1-25], alkynyl [$C_mH_{2m-3}$ where m=1-25], mono-, di-, and tri-substituted, $C_6H_{5-n}R_n$, mono, di, or poly substituted naphthyl $C_{10}H_{8-n}R_n$, mono, di, or poly substituted anthryl $C_{14}H_{10-n}R_n$, mono, di or poly substituted phenanthryl $C_{14}H_{10-n}R_n$, polycondensed aromatic, $C_{16}H_{10}R_n$ and the like, F, Cl, Br, I, $C_mH_{2m+2-x}M_x$ where M=F, Cl, Br, I, and x=1-25, thiophenol, thioether [S—$R_6$ where $R_6$ is linear or branched alkyl [$C_mH_{2m+1}$ where m=1-25], cycloalkyl [$C_mH_{2m-1}$ where m=1-25] alkenyl [$C_mH_{2m-1}$ where m=1-25], cycloalkyl [$C_mH_{2m-1}$ where m=1-25] alkynyl [$C_mH_{2m-3}$ where m=1-25], mono-, di-, and tri-substituted, $C_6H_{5-n}R_n$, mono, di, or poly substituted naphthyl $C_{10}H_{8-n}R_n$, mono, di or poly substituted anthryl $C_{14}H_{10-n}R_n$, mono, di or poly substituted phenanthryl $C_{14}H_{10-n}R_n$, polycondensed aromatic, $C_{16}H_{10}R_n$ and the like, amino [$NR_7R_8$ where $R_7$ and $R_8$ are the same or different and are H or linear or branched alkyl [$C_mH_{2m+1}$ where m=1-25], cycloalkyl [$C_mH_{2m-1}$ where m=1-25] alkenyl [$C_mH_{2m-1}$ where m=1-25], alkynyl [$C_mH_{2m-3}$ where m=1-25], mono-, di-, and tri-substituted, $C_6H_{5-n}R_n$, mono, di, or poly substituted naphthyl $C_{10}H_{8-n}R_n$, mono, di, or poly substituted anthryl $C_{14}H_{10-n}R_n$, mono, di or poly substituted phenanthryl $C_{14}H_{10-n}R_n$, polycondensed aromatic, $C_{16}H_{10}R_n$ and the like, piperidino, morpholino, pyrryl, ammonium, [$NR_4^+$], amido [—$NR_2$C(=O)—], ester, [—COO$R_n$], sulfonamide [—SON$R_2$], aldehyde —[CHO], ketone [—C(=O)R] one or more heterocyclic groups that may or may not be alkylated including thiophene, furan, indole, benzo[b]thiophene, benzo[c]thiophene, benzo[b]furan, benzo[c]furan, indole, heterocyclic groups with two or more heteroatoms, and the like. The group might also consist of substituent(s) (C1-C10)alkyl, acryloxy, methacryloxy, chloro and fluoro. $R_n$ may also be polymeric including poly (ethylene), poly(isopropenyl), poly(propylene), poly(butadienyl), poly(styryl), poly(acylate), poly(methacrylate), poly (fluorocarbon), poly(chlorocarbon) and the like.

Appendix 2

Light Sources

It is also the purpose of the patent to teach that though sunlight may be used as the source of UV-A, and in part, UV-B if that is necessary, artificial light sources may be preferred. These artificial sources include commercial light sources like mercury resonance lamps and electrode-less discharge lamps, as well as light emitting diodes (LED's) that produce either visible or UV light. A partial table of such sources is shown below.

| Artificial Light Sources Comparison of Different Light Sources | | |
|---|---|---|
| Light Source | Dose, mW/cm$^2$ | Comments |
| 395 nm 5 mm LED | 57 | Inexpensive 5 mm LED |
| PLLS-1 Prototype | 49 | WPL developed light source prototype |
| UVPC Source | 132 | Commercial source by UV Process |
| Xe-500B Lamp | 121 | Industrial Xe lamp |
| 3M Overhead Proj. | 526 | Standard overhead projector |

-continued

Artificial Light Sources
Comparison of Different Light Sources

| Light Source | Dose, mW/cm² | Comments |
|---|---|---|
| 250 PMP UV Lamp | 1400 | Industrial UV curing lamp |
| EFOS Ultracure | 594 | Commercial blue light source |
| Fusion H-bulb | 1346 | Popular industrial curing source |
| THC³ Blue LED | 367 | Ultrabright 5 mm LED |
| THC³ Green LED | 93 | Ultrabright 5 mm LED |
| THC³ Red LED | 144 | Ultrabright 5 mm LED |
| LIII R. Blue Emitter | 521 | High intensity emitter |
| LIII Blue Emitter | 328 | High intensity emitter |
| LIII Green Emitter | 171 | High intensity emitter |
| LIII Red Emitter | 581 | High intensity emitter |

Appendix 3

Uses for Aromatic Byproducts

The aromatic ketone(s) produced in the decomposition reaction, the so-called acetophenones or their congeners have a plethora of uses such as for termite control Naphthalene derivatives as termite repellents and termiticides. Henderson, Gregg; Ibrahim, Sanaa A.; Patton, Rosemary; Laine, Roger A.; Zhu, Betty C. R.; Chen, Feng. (USA). U.S. Pat. Appl. Publ. (2005), 25 pp. CODEN: USXXCO US 2005037045 A1 20050217 Patent written in English. Application: US 2003-641315 20030814. CAN 142:192781 AN 2005:140565 CAPLUS as drug delivery carriers as in 20040235691

Nonbar personal product compositions comprising crystalline wax structured benefit agent premix or delivery vehicle Pham, Quynh; (Murray Hill, N.J.); O'Connor, Stephen M.; (New York, N.Y.); Glynn, John R. JR.; (Westfield, N.J.); Lips, Alexander; (Edgewater, N.J.), in the synthesis of electronic materials as in Synthesis of polyphenylenes from acetylaromatic compounds. Shmakova, O. E.; Khotina, I. A.; Nikonova, S, N.; Rusanov, A. L.; Teplyakov, M. M. Inst. Elementoorg. Soedin. im. Nesmeyanova, Moscow, Russia. Vysokomolekulyarnye Soedineniya, Seriya B: Kratkie Soobshcheniya (1992), 34(10), 36-44. CODEN: VYSBAI ISSN: 0507-5483. Journal written in Russian.

Curing of polyphenylenes based on acetylaromatic compounds in the presence of organosilazanes. Teplyakov, M. M.; Shmakova, O. E.; Khotina, I. A.; Izmailov, B. A.; Rusanov, A. L. Inst. Elementoorg. Soedin. im. Nesmeyanova, Moscow, Russia. Vysokomolekulyarnye Soedineniya, Seriya A (1992), 34(10), 23-30. CODEN: VYSAAF ISSN: 0507-5475. Journal written in Russian. CAN 119:96930 AN 1993:496930 CAPLUS Polyphenylenes from ketals of acetylaromatic compounds with reactive furfurylidene and nitrile groups. Korshak, V. V.; Teplyakov, M. M.; Dmitrenko, A. V.; Kakauridze, D. M. Inst. Elementoorg. Soedin., Moscow, USSR. Vysokomolekulyarnye Soedineniya, Seriya A (1980), 22(2), 256-61. CODEN: VYSAAF ISSN: 0507-5475. Journal written in Russian. CAN 92:181933 AN 1980: 181933 CAPLUS Production of Aromatic acetal compound JP2115140A 1990-04-27JP2600858B2 B2 1997-04-16 And Preparation of Acetylaromatics from Isopropenyl Compounds. Kondo, Masahiro; Tanaka, Michio; Taniguchi, Katsuo. (Mitsui Petrochemical Industries, Ltd., Japan). Jpn. Kokai Tokkyo Koho (1990), 4 pp. CODEN: JKXXAF JP 02115140 A2 19900427 Heisei. Patent written in Japanese. Application: JP 88-267637 19881024. CAN 113:131744 AN 1990:531744 CAPLUS And as hair restorers "Hair restorer". Christen, A. (1926), GB 264862 19260121 Patent language unavailable. CAN 22:2615 AN 1928:2615 CAPLUS Methyl ketones, which may be produced by the Norrish Type II reaction also have many uses including as Antibotulinal properties of selected aromatic and aliphatic ketones. Bowles, Bobby L.; Miller, Arthur J. East. Reg. Res. Cent., U.S. Dep. Agric., Philadelphia, Pa., USA. Journal of Food Protection (1993), 56(9), 795-800. CODEN: JFPRDR ISSN: 0362-028X. Journal written in English. CAN 120: 161981 AN 1994:161981 CAPLUS Analysis of] vanilla extracts and imitations. Ensminger, Luther G. Food & Drug Admin., Los Angeles, Calif., Journal of the Association of Official Agricultural Chemists (1957), 40 423-33. CODEN: JOACAZ ISSN: 0095-9111. Journal language unavailable. CAN 51:48670 AN 1957:48670 CAPLUS to make aromatherapy oils such as in the case of, but not limited to the case of, piperonyl methyl ketone and cedryl methyl ketone. Ketones synthesized by the Norrish Type II reaction producing such products will be preferred.

Appendix 4

Other Addition Reactions of Hydroperoxides to Olefins

Organic peroxides. XIV. Base catalyzed addition of hydroperoxides on aryl(vinyl)sulfones. Kropf, Heinz; Ball, Michael; Hofmann, Klaus. Inst. Org. Chem. Biochem., Univ. Hamburg, Hamburg, Fed. Rep. Ger. Justus Liebigs Annalen der Chemie (1976), (12), 2316-24.

Organic peroxides. X. Base-catalyzed addition of hydroperoxides to oxiranes. Kropf, H.; Ball, M.; Schroeder, H.; Witte, G. Inst. Org. Chem., Univ. Hamburg, Hamburg, Fed. Rep. Ger. Tetrahedron (1974), 30(16), 2943-8.

Dioxododecenoic Acid: A Lipid Hydroperoxide-Derived Bifunctional Electrophile Responsible for Etheno DNA Adduct Formation. Lee, Seon Hwa; Elipe, Maria V. Silva; Arora, Jasbir S.; Blair, Ian A. Center for Cancer Pharmacology, University of Pennsylvania School of Medicine, Philadelphia, Pa., USA. Chemical Research in Toxicology (2005), 18(3), 566-578.

Preparation of Cycloalkanols and Cycloalkanones from Cycloalkyl Hydroperoxides. Hamamoto, Shunichi; Yamanaka, Mitsuo; Nakamura, Takahito; Shimano, Tetsuro. (Ube Industries, Ltd., Japan). Jpn. Kokai Tokkyo Koho (1997), 5 pp. CODEN: JKXXAF JP 09077704 A2.

Multidipole effect in addition reactions of oxygen, cumyl hydroperoxide, and cumylperoxy radical to the double bond of pentaerythritol monoacrylate tripropionate. Sokolov, A. V.; Pliss, E. M.; Denisov, E. T. Inst. Khim. Fiz., Chemogolovka, USSR. Izvestiya Akademii Nauk SSSR, Seriya Khimicheskaya (1988), (2), 293-7.

Formation of hydroperoxides with unconjugated diene systems during autoxidation and enzymic oxygenation of linoleic acid. Haslbeck, Franz; Grosch, Werner; Firl, Joachim. Dtsch. Forschungsanst. Lebensmittelchem., TU Muenchen, Garching, Fed. Rep. Ger. Biochimica et Biophysica Acta (1983), 750(1), 185-93.

Reversal of stereospecificity during allylic hydroperoxidation of 3-norcarene and bicyclo[4.2.0]oct-3-ene derivatives arising from structurally enforced quenching of singlet oxygen by the hydrazide functionality. Paquette, Leo A.; Liao, C. C.; Liotta, Dennis C.; Fristad, William E. Evans Chem. Lab., Ohio State Univ., Columbus, Ohio, USA. Journal of the American Chemical Society (1976), 98(20), 6412-13.

Addition of N-acetylcysteine to linoleic acid hydroperoxide. Gardner, H. W.; Weisleder, D.; Kleiman, R. NRRL, ARS, Peoria, Ill., USA. Lipids (1976), 11(2), 127-34.

Addition of hydroperoxides to N-vinyl compounds. Lederer, Michael. Farbwerke Hoechst A.-G., Frankfurt/M.-Hoechst, Fed. Rep. Ger. Chemische Berichte (1972), 105(7), 2169-74.

In situ olefin-derived peroxides. Effectiveness for initiating radical addition and polymerization reactions. Norton, Charles J.; Dormish, Frank L.; Reuter, Michael J.; Seppi, Ned F.; Beazley, Phillip M. Denver Res. Cent., Marathon Oil Co., Littleton, Colo., USA. Industrial & Engineering Chemistry Product Research and Development (1972), 11(1), 27-35.

Stereochemistry of the addition of tert-butyl hydroperoxide to cyclopentadiene. Haubenstock, H.; Mennitt, P. G.; Butler, Peter E. Richmond Coll., City Univ. of New York, Staten Island, N.Y., USA. Journal of Organic Chemistry (1970), 35(10), 3208-10.

Addition of tert-butyl hydroperoxide to isoolefins. Antonovskii, V. L.; Emelin, Yu. D. USSR. Editor(s): Emanuel, N. M. Usp. Khim. Org. Perekisnykh Soedin. Autookisleniya, Dokl. Vses. Konf., 3rd (1969), Meeting Date 1965, 310-13. Publisher: Izd. "Khimiya", Moscow, USSR.

What is claimed is:

1. A method comprising:
    synthesizing a hydrocarbon from a natural oil containing a fatty acid or a fatty acid derivative wherein the step of synthesizing comprises converting the fatty acid or the fatty acid derivative to a photoactive specie, and irradiating the photoactive specie to undergo its decomposition to the hydrocarbon by a Norrish Type II reaction.

2. The method of claim 1 wherein the converting step comprises:
    reacting the fatty acid or the fatty acid derivative with an aromatic compound to produce an aryl fatty ketone as the photoactive specie, and the step of irradiating comprises irradiating the aryl fatty ketone with radiation that causes the ketone to decompose and form an olefin as the hydrocarbon.

3. The method of claim 2 in which the method further comprises the step of hydrogenating the fatty acid when the fatty acid is an unsaturated fatty acid.

4. The method of claim 2 in which the aryl fatty ketone is produced from the fatty acid or derivative by a Friedel-Crafts reaction.

5. The method of claim 4 in which the aryl fatty ketone comprises a moiety that is reactive in a n-π* photoreduction sequence.

6. The method of claim 2 in which the aryl fatty ketone is sensitized to a reactive excited state.

7. The method of claim 6 in which the sensitizer is selected from the group consisting of acetophenone, propiophenone, benzoic acid and derivatives thereof, benzonitrile and derivatives thereof, phenols, anilines, benzimidazole, pyridines, benzene and substituted benzenes, phenyl acetic acid, phenyl propionoic acid, methyl acrylate, methyl methyl acrylate, and polymers derived therefrom.

8. The method of claim 1 wherein the photoactive species is a fatty alkanone.

9. The method in claim 8 in which the fatty acid or the fatty acid derivative is reacted with any alcohol.

10. The method of claim 8 in which the fatty acid or the fatty acid derivative is reacted with any polymeric alcohol.

11. The method of claim 8 in which the fatty acid or the fatty acid derivative is reacted with any phenol.

12. The method of claim 8 in which the fatty alkanone is sensitized to a reactive excited state.

13. The method of claim 1 wherein the photoactive specie is a fatty acid ester.

14. The method of claim 13 in which the ester irradiated is a methyl-ester.

15. The method of claim 13 in which the ester irradiated is biodiesel.

16. The method of claim 13 in which the ester irradiated is an aromatic ester.

17. The method of claim 13 in which the fatty acid ester is sensitized to a reactive excited state.

18. The method of claim 1 wherein the photoactive specie is a fatty acid amide.

19. The method of claim 18 in which the fatty acid or the fatty acid derivative is reacted with an alkylamine.

20. The method of claim 18 in which the fatty acid or the fatty acid derivative is reacted with an arylamine.

21. The method of claim 18 in which the fatty acid or the fatty acid derivative is reacted with a polymeric amine.

22. The method of claim 18 in which the fatty acid amide is sensitized to a reactive excited state.

23. The method of claim 1 in which the natural oil is a vegetable oil.

24. The method of claim 1 in which the natural oil is selected from the group consisting of peanut, soy, corn, sunflower, safflower, tong, linseed, hemp, coconut, and mixtures thereof.

25. The method of claim 1 in which the fatty acid is selected from the group consisting of palmitic, stearic, oleic, linoleic and linolenic acid and mixtures thereof.

26. The method of claim 1 wherein the natural oil is a vegetable oil derived from peanut, corn, sunflower, safflower, tong, linseed, hemp, coconut, and mixtures thereof and the photoactive specie is an aryl fatty ketone.

27. The method of claim 26 wherein the aryl fatty ketone is an aryl alkyl fatty ketone in which the alkyl group is a palmito, stearo, oleo, linoleo, or linolenyl.

28. The method of claim 27 in which the aryl alkyl fatty ketone comprises two alkyl groups selected from palmito, stearo, oleo, linoleo, or linolenyl.

29. A method for synthesizing hydrocarbons from natural renewable resources and materials, the method comprising:
    converting a fatty acid or fatty acid derivative contained in a natural renewable resource or a natural renewable material into a photoactive specie; and
    exposing the photoactive specie to UV radiation such that it degrades into at least one hydrocarbon by a Norrish Type II reaction.

30. The method of claim 29 in which the UV radiation is from an artificial source.

31. The method of claim 29 in which the UV radiation is from a lamp.

32. The method of claim 29 in which the UV radiation is from a light emitting diode (LED) or an array of light emitting diodes.

33. The method of claim 29 in which the UV radiation is UV-C radiation.

* * * * *